(12) United States Patent
Petkov et al.

(10) Patent No.: US 10,487,294 B2
(45) Date of Patent: Nov. 26, 2019

(54) COMPOSITIONS WITH REDUCED DYE-TRANSFER PROPERTIES

(71) Applicant: Conopco, Inc., Englewood Cliffs, NJ (US)

(72) Inventors: Jordan Todorov Petkov, Petaling Jaya (MY); Paul Simon Stevenson, Liverpool (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/552,672

(22) PCT Filed: Feb. 9, 2016

(86) PCT No.: PCT/EP2016/052680
§ 371 (c)(1),
(2) Date: Aug. 22, 2017

(87) PCT Pub. No.: WO2016/139032
PCT Pub. Date: Sep. 9, 2016

(65) Prior Publication Data
US 2018/0044612 A1    Feb. 15, 2018

(30) Foreign Application Priority Data
Mar. 2, 2015 (EP) .................................. 15157244

(51) Int. Cl.
| | | |
|---|---|---|
| *C11D 1/00* | (2006.01) | |
| *C11D 3/00* | (2006.01) | |
| *A61Q 5/00* | (2006.01) | |
| *A61K 8/99* | (2017.01) | |
| *C11D 1/36* | (2006.01) | |
| *C11D 1/06* | (2006.01) | |
| *A61K 8/60* | (2006.01) | |
| *C11D 1/66* | (2006.01) | |

(52) U.S. Cl.
CPC ............ *C11D 3/0021* (2013.01); *A61K 8/602* (2013.01); *A61K 8/99* (2013.01); *A61Q 5/004* (2013.01); *C11D 1/06* (2013.01); *C11D 1/36* (2013.01); *C11D 1/662* (2013.01)

(58) Field of Classification Search
CPC .............................. A61Q 5/004; C11D 3/0021
See application file for complete search history.

(56) References Cited

U.S. PATENT DOCUMENTS

| | | |
|---|---|---|
| 2,182,306 A | 12/1939 | Ulrich |
| 2,208,095 A | 7/1940 | Easelmann et al. |
| 2,553,696 A | 5/1951 | Wilson |
| 2,806,839 A | 9/1957 | Crowther et al. |
| 3,033,746 A | 5/1962 | Moyle et al. |
| 5,578,563 A | 11/1996 | Trinh et al. |
| 5,656,747 A | 8/1997 | Mixich et al. |
| 6,077,816 A | 6/2000 | Puvvada et al. |
| 6,903,064 B1 | 6/2005 | Kasturi et al. |
| 2004/0171512 A1 | 2/2004 | Furuta et al. |
| 2004/0091446 A1 | 5/2004 | Massaro et al. |
| 2004/0136942 A1 | 7/2004 | Yamazaki |
| 2004/0152613 A1 | 8/2004 | Develter et al. |
| 2006/0183662 A1 | 8/2006 | Crotty et al. |
| 2006/0287216 A1 | 12/2006 | Song |
| 2007/0079446 A1 | 4/2007 | Lupia et al. |
| 2012/0322751 A1 | 12/2012 | Piljac |
| 2013/0053295 A1 | 2/2013 | Kinoshita et al. |
| 2013/0072414 A1* | 3/2013 | Price ...................... C11D 1/37 510/220 |
| 2014/0086864 A1 | 3/2014 | Ishimori et al. |
| 2016/0081890 A1 | 3/2016 | Stevenson |
| 2018/0044614 A1 | 2/2018 | Jones et al. |

FOREIGN PATENT DOCUMENTS

| | | |
|---|---|---|
| CN | 101407831 | 4/2008 |
| DE | 4237334 | 5/1994 |
| DE | 19648439 | 5/1998 |
| DE | 102009046169 | 5/2011 |
| EP | 0317036 | 5/1989 |
| EP | 0975718 | * 2/2000 |
| EP | 1411111 | 4/2004 |
| EP | 1445302 | 8/2004 |
| EP | 2410039 | 1/2012 |
| WO | WO9838270 | 9/1998 |
| WO | WO2006086492 | 8/2006 |
| WO | WO2011117427 | 9/2011 |
| WO | WO2011120776 | 10/2011 |
| WO | WO2012010406 | 1/2012 |
| WO | WO2012156250 | 11/2012 |

(Continued)

OTHER PUBLICATIONS

Heyd et al., Development and trends of biosurfactant analysis and purificaiton using rhamnolipids as an example, Analytical and Bioanalytical Chemistry, Mar. 6, 2008, pp. 1579-1590, 391-5 (NPL 1, pp. 1-12).

(Continued)

*Primary Examiner* — Eisa B Elhilo
(74) *Attorney, Agent, or Firm* — Greenberg Traurig, LLP

(57) ABSTRACT

A method of protecting a colored or dyed substrate from dye transfer during exposure to aqueous cleansing solutions, the method comprising the step of treating said a dyed or colored substrate with a composition comprising a surfactant system, wherein said system comprises a biosurfactant in the range 50-100 wt. % of the total surfactant system.

11 Claims, No Drawings

(56) References Cited

FOREIGN PATENT DOCUMENTS

| WO | WO2013043857 | 3/2013 |
|----|--------------|--------|
| WO | WO2014095367 | 6/2014 |
| WO | WO2014118095 | 8/2014 |
| WO | WO2014173659 | 10/2014 |

OTHER PUBLICATIONS

IPRP in PCTEP2016053982, Feb. 3, 2017 (NPL 1, pp. 13-26).
IPRP2 in PCTEP2016052680, May 19, 2017 (NPL 1, pp. 27-45).
Reiling et al., Pilot plant production of rhamnolipid biosurfactant by Pseudomonas aeruginosa, Applied and Environmental Microbiology, May 1986, pp. 985-989; XP055036395 retrieved from internet: http://aem.asm.org/content/51/5/985.full.pdf, 51-5 (NPL 1, pp. 46-51).
Search Report & Written Opinion in PCTEP2016054025, dated Jun. 1, 2016 (NPL 1, pp. 52-62).
Search Report and Written Opinion in PCTEP2016052680, dated Apr. 18, 2016 (NPL 1, pp. 63-76).
Search Report and Written Opinion in PCTEP2016053982, dated May 17, 2016, WO (NPL 1, pp. 77-90).
Search Report and Written Opinion in EP15157240, dated Aug. 18, 2015 (NPL 2, pp. 1-5).
Search Report and Written Opinion in EP15157241, dated Jul. 24, 2015, EP (NPL 2, pp. 6-14).
Search Report and Written Opinion in EP15157244, dated Aug. 26, 2015 (NPL 2, pp. 15-22).
Written Opinion 2 in PCTEP2016052680, dated Feb. 23, 2017 (NPL 2, pp. 23-29).
Co-pending Application Marriott et al., Filed Aug. 22, 2017.
Co-pending Application Jones et al., Filed Aug. 22, 2017.
Chemical Engineering; Supercritical CO2: A Green Solvent; Chemical Engineering; 2010; 1-7.
Elhenshir et al.; Supercritical carbon dioxide as green product for effective environmental remediation; Energy Procedia; 2013; 6964-6978; vol. 37.
Tena et al.; Supercritical fluid extraction of t-resveratrol and other phenolics from a spiked solid; J Anal Chem; 1998; 143-148; vol. 361.
Novik et al.; A novel procedure for the isolation of glycolipids from Bifodabacterium adolescentis 94 BIM using supercritical carbon dioxide; Journal of Biotechnology; 2006; 555-562; vol. 121.
Montanari et al.; Selective extraction of phospholipids from soybeans with supercritical carbon dioxide and ethanol; The Journal of Supercritical Fluids; 1999; 87-93; vol. 14.
S.S. Helvaci et al.; Effect of electrolytes on the surface behavior of rhamnolipids R1 and R2; Colloids and Surfaces B: Biointerfaces; 2004; pp. 225-233; vol. 35; Elsevier.

* cited by examiner

COMPOSITIONS WITH REDUCED DYE-TRANSFER PROPERTIES

This invention relates to compositions for use in aqueous based treatments of coloured or dyed substrates such as fabrics and dishes, with reduced dye transfer.

In certain washing situations dye-loss or dye-fade is undesirable such as the washing of bright/dark fabrics or dyed hair in which wanted dyes are transferred to the washing solution and e.g. in fabric washing, from the substrate to other substrates.

An object of the invention is to provide a composition and a process for personal bathing and hand washing of dishes and/or fabrics with reduced dye-transfer.

According to a first aspect of the present invention there is provided a method of protecting a coloured or dyed substrate from dye transfer during exposure to an aqueous cleansing solution, the method comprising the step of treating a dyed or coloured substrate with a composition comprising a surfactant system, wherein said surfactant system comprises a biosurfactant in the range 50-100 wt. % (of the total surfactant system).

Preferably, the biosurfactant is a glycolipid.

Preferably, the amount of biosurfactant in the composition is in the range 50-100 wt. % of the total surfactant system.

Preferably, the surfactant system constitutes the sole surfactant content of the composition.

According to a further aspect of the present invention there is provided use of a washing composition comprising a glycolipid biosurfactant to reduce dye transfer from a coloured or dyed substrate during a washing process.

The substrate is preferably a fabric or hard surface or hair which is coloured or dyed. The colour/dye may be natural or may result from artificial colouring with dyes or pigments or combinations thereof.

In a further aspect of the invention there is provided, a cleaning composition for use in the above method the composition comprising a surfactant system comprising a glycolipid biosurfactant which is present at a level of 50%-100 wt. % of the total surfactant in said surfactant system.

Preferably, the amount of biosurfactant in the composition is in the range 50-100 wt. % of the total surfactant system. Preferably, the surfactant system constitutes the sole surfactant content of the composition.

Preferably the glycolipid biosurfactant comprises a rhamnolipid.

Preferably the glycolipid biosurfactant comprises a sophorolipid. If sophorolipids are included, acidic forms of sophorolipids are preferred.

The glycolipid biosurfactant may comprise combinations of different glycolipid biosurfactants.

In the case of rhamnolipids, throughout this patent specification, the prefixes mono- and di- are used to indicate respectively to indicate mono-rhamnolipids (having a single rhamnose sugar ring) and di-rhamnolipids (having two rhamnose sugar rings) respectively. If abbreviations are used R1 is mono-rhamnolipid and R2 is di-rhamnolipid. Preferably the ratio of R1:R2 is such that R2 is always greater in proportion to R1, and more preferably the rhamnolipid is 100 wt. % R2.

Preferably the glycolipid is present at 75-95 wt. % of the surfactant combination.

Most preferably the glycolipid biosurfactant is a rhamnolipid present at 75-95 wt. %

The surfactant combination preferably comprises a synthetic anionic surfactant. 'Anionic surfactants' are defined herein as amphiphilic molecules comprising one or more functional groups that exhibit a net anionic charge when in aqueous solution at the normal wash pH of between 4 and 11.

Preferably the alkali metal salts of organic sulphur reaction products having in their molecular structure an alkyl moiety containing from about 6 to 24 carbon atoms, more greater than 12 carbon atoms and preferably also a moiety selected from the group consisting of sulphonic and sulphuric acid ester moieties. Additionally or alternatively, the anionic surfactant preferably has low levels of ethoxylation, preferably comprising 1-12 ethylene oxide units per molecule, more preferably 1-3 and even more preferably 1. The units of ethylene oxide may be an average.

Providing the formulation scientist with the freedom to use longer carbon chain lengths and/or lower levels of ethoxylation is greatly beneficial, not least on cost grounds. However these factors increase calcium intolerance and so such surfactants are advantageous selections for the present invention.

Although any anionic surfactant hereinafter described can be used, such as primary alkyl sulphates (PAS) e.g. sodium lauryl sulphate (SLS) and e.g. alkyl ether sulphate such as sodium lauryl ether sulphate (SLES), soaps, fatty acid ester sulphonates, fatty acid sulphates or sulphonates; alkyl benzene sulphonates (LAS), sulphosuccinate esters, olefin sulphonates, paraffin sulphonates and organic phosphates; fatty alcohol sulphates; alkyl phenol ether sulphate; fatty acyl isethionate products which products comprise fatty acyl isethionate and free fatty acid and/or fatty acid salt; alkyl sulphonates such as sodium alkane sulphonate. Preferred anionic surfactants are the alkali (ammonium or triethylammonium for example) and alkaline earth metal salts of the above. The source oil/alcohol can be plant or animal derived for example coconut or palm or tallow etc.

The surfactant system is present in the fabric or hard surface washing compositions at a level of from 3 to 85% by weight, preferably from 3 to 60% by weight, more preferably from 3 to 40% by weight, most preferably from 3 to 35% by weight.

The surfactant system is present in personal (human skin and hair) wash compositions at a level of 5 to 60%, preferably 10 to 40% surfactant, while cosmetic compositions need not comprise any surfactant, but preferably comprise 1% to 30% by wt., more preferably 1 to 15% by wt. surfactant.

The compositions of the invention may comprise other ingredients as described hereinbelow.

Hand washing and fabric cleaning compositions may comprise polyester substantive soil release polymers, hydrotropes, opacifiers, colorants, other enzymes, further surfactants such as non-ionic, cationic and or amphoteric surfactants, microcapsules of ingredients such as perfume or care additives, softeners, polymers for anti re-deposition of soil, bleach, bleach activators and bleach catalysts, antioxidants, pH control agents and buffers, thickeners, external structurants for rheology modification, visual cues, either with or without functional ingredients embedded therein and other ingredients known to those skilled in the art.

The compositions of the invention comprise pourable liquids and preferably have a viscosity in the range 250 to 100,000 mPas (cP) measured at a shear rate 10 s@-1 and 25 DEG C., in a Haake Rotoviscometer RV20.

Shampoo compositions are preferably in the range from 5000 to 8000 Cp.

Compositions of the invention may be formulated as products for washing fabrics, skin or hair and may include rinse-off, wipe-off and leave-on care products.

The composition is preferably a liquid, gel but may also be a free flowing particulate, paste, or tabletted.

The invention will be further described with reference to the following non-limiting examples.

EXAMPLES LAUNDRY FORMULATION

Examples 1 and 2

| OOA | Name | SUPPLIER | EG 1 as 100% (%) | EG 2 as 100% (%) |
|---|---|---|---|---|
| 1 | Demin water | Demin water | 27.28 | 27.28 |
| 2 | Tinopal CBS-SP | Ciba | 0.25 | 0.25 |
| 3 | Mono Propylene Glycol MPG | Dow | 8 | 8 |
| 4 | Neodol 25_7 | Shell | 5.04 | 0 |
| 5 | Acusol 820 | Dow | 1 | 1 |
| 6 | Mono ethanol amine | Dow | 6.2 | 6.2 |
| 7 | EU LAS acid - Petresa HF | Petresa HF plus PSU Sulphonation | 6.72 | 0 |
| 8 | Rhamnolipid - JBR425 - Jeneil | Jeneil | 11.2 | 28 |
| 9 | Tri ethanol amine | Dow | 4.035 | 4.035 |
| 10 | Citric Acid | Tate and Lyle | 2.5 | 2.5 |
| 11 | Prifac 5908 | Palmera B1231 - | 3.5 | 3.5 |
| 12 | Dequest 2010 | ex Thermophos | 1.5 | 1.5 |
| 13 | Sodium Sulphite - | Aldrich | 0.25 | 0.25 |
| 14 | EU SLES 3EO - | PSU Sulphonation (synthetic source) | 5.04 | 0 |
| 15 | Sokolan HP20 | BASF | 2 | 2 |
| 16 | Perfume | IFF | 1.39 | 1.39 |
| 17 | Acusol OP301 | Acusol OP301 - Dow o | 0.1 | 0.1 |

Notes For Examples 1 and 2:
OOA is the order of addition upon making the formulation
Tinopal CBS SP Slurry 33 a Distyryl biphenyl derivative CAS No. 27344-41-8
Acusol 820, a copolymer of acrylic acid with C18 and with EO20C18 side chains, MW about 500,000
Prifac 5908 is Hydrogenated Topped Palm Kernel Fatty Acids=
Dequest 2010 is 1-Hydroxyl ethylidene-1,1,-diphosphonic acid, HEDP
Sokolan HP20 is ethoxylated polyethylene imine
Neodol 25-7 is is a primary C12-C15 Alcohol Ethoxylate with average of 7 moles of ethylene oxide per mole of alcohol
Acusol 820 is Hydrophobically modified Alkali soluble acrylic polymer emulsion
EU LAS is Linear Alkyl Benzene Sulphonate
SLES 3EO is Sodium Lauryl Ether Sulphate with average distribution of 3 moles of ethylene oxide per mole of Sodium Lauryl Sulphate
Rhamnolipid JBR 425 is A mixture of mono and Di rhamnolipids where the IUPAC name for mono rhamnolipid is 3-[3-[(2R,3R,4R,5R,6S)-3,4,5-trihydroxy-6-methyloxan-2-yl]oxydecanoyloxy]decanoic acid and Di rhamnolipid is - 3-[3-[4,5-dihydroxy-6-methyl-3-(3,4,5-trihydroxy-6-methyloxan-2-yl)oxyoxan-2-yl]oxydecanoyloxy]decanoic acid
Soladona 2012 is perfume supplied by IFF
Accusol OP301 = Is an opacifier supplied as an emulsion

Examples 3-6

Hair Compositions

| INCI name | Tradename | Ex 3 wt. % | Ex 4 wt. % | Ex 5 wt. % | Ex 6 wt. % |
|---|---|---|---|---|---|
| ethoxylated alkyl sulfate anionic surfactant having an average degree of ethoxylation of from 0.5 to 3, preferably 1 to 3 and most preferably 1. | Texapon N701 | 4.0 | 10.0 | 10.0 | 6.0 |
| BIOSURFACTANT [4] | | 4.0 | 5.0 | 5.0 | 3.0 |
| Cocamidopropyl Betaine | Tegobetaine CK | 3.0 | 3.0 | 1.6 | 3.0 |
| Fatty Acyl Isethionate Product[1] (DEFI) | Unilever | 7.0 | 2.0 | 4.0 | 3.0 |
| Sodium Cocoyl Isethionate | Jordapon CI | — | — | — | 3.0 |
| Carbomer | Carbopol 980 | 0.60 | 0.60 | 0.60 | 0.60 |
| Silicone Oil[2] | | 2.2 | 2.2 | 2.2 | 2.2 |
| Guar Hydroxypropyltrimonium Chloride | BFG-Jaguar C17 | 0.25 | 0.25 | 0.25 | 0.25 |
| Parfum | Snow White - Givaudan | 0.75 | 0.75 | 0.75 | 0.75 |
| Aqua + minors | Water + minors | to 100 | to 100 | to 100 | to 100 |

[1]The Fatty Acyl Isethionate product is Sodium Cocoyl isethionate, Stearic Acid, Coconut Fatty Acid, Sodium Isethionate and Water produced in-house by Unilever
[2]Mixture of silicone emulsions from Wacker and Dow
[3] The Viscosity of the formulations was measured using a Brookfield viscometer at 30° C. and 20 rpm using spindle N5; all were in the range of from 5000 to 8000 Cp
[4] The biosurfactant is Rhamnolipid JBR425 (CAS no. 147858-26-2) ex. Jeneil Biosurfactant Co., LLC

Experimental

The following experiment was carried out to assess the removal of hair dye from dyed hair swatches by different surfactant systems in solution.

Method

The method measures absorbance, at a wavelength that corresponds to the concentration of dye in solution, of a supernatant solution. The supernatant solution is produced after soaking dyed hair swatches in various detergent solutions that are made up either with or without the presence of Biosurfactants in a controlled test. The lower the absorbance the less amount of dye remains in the supernatant solution and consequently is indicative of less removal of dye from the hair swatch.

Materials
SLES—1EO—Texapon N71—Shell
JBR425—Rhamnolipid—Jeneil
Permanent Hair colourant—having a shade level 1 (black) or 2 (darkest brown) according to the International Colour Chart (ICC).

Colour Loss Method
 2.5 g 6" hair switches previously bleached * were dyed using a commercially available permanent colourant
 10 g of the colourant were applied to the hair switch and rubbed through for 30 seconds using a brush until colour is evenly distributed.
 The switch was then left for 35 minutes before rinsing for 2 minutes under controlled temperature (37° C.) and flow (4 L/min).
 150 g of the bio-surfactant and/or synthetic Surfactant solutions or combination of (as outlined in the results section under the title surfactant) were prepared at 1% w/w and the switch was then placed into the surfactant solution and left for 1 hour at ambient temperature.
 After 1 hour, the switch was removed from the surfactant. A sample of the resulting solution was then added to a cuvette and the absorbance measured with a Jasco 600 UV spectrometer at a set wavelength of 522 nm.

Preparation of Switches—Bleaching
Equipment Required
L'Oreal Platine Precision Powder Bleach
Excel Crème Peroxide—9% Vol
Tinting Bowl
Tinting Brush
Aluminium Foil
Stop clock All rinsing and washing to be done using the flow/temperature controlled taps. The flow rate is set at 4 liters/minute and a temperature of 35° C.-40° C.

| Number of Switches | Type of Switch | Amount of Bleach Powder (g) | Amount of Peroxide (g) |
|---|---|---|---|
| 4 | 10" | 60 | 120 |
| 5 | 6" | 30 | 60 |

First bleach application . . .

1. Lay out four sheets of Aluminium Foil on the bench large enough to allow for the switch to be wrapped in the foil to develop once the bleach has been applied.
2. Weigh out the bleach powder into a tinting bowl.
3. Weigh out the crème peroxide by gently pouring it over the powder so that the powder is completely submerged. Mix into a creamy consistency Using an IKA-WERKE Eurostar Power Control-Visc Overhead Stirrer with a whisk attached. Mix for 60 seconds at 400 rpm. The tinting bowl must be held firmly flat in place. Ensure that there are no lumps as this will give an uneven colour on the switches. Once the mixture is prepared it must be used immediately.
4. Spread one of the switches (in a fan shape) on the sheet of foil.
5. Apply the bleach mixture with a tinting brush. Ensure even coverage of the switch by turning it and applying the bleach to each side twice.

Side 1 apply for 45 seconds, turn over
Side 2 apply for 45 seconds, turn over
Side 1 apply for 45 seconds, turn over
Side 2 apply for 45 seconds 6. Bring the hair fibres together and leave the switch in its normal shape, wrap the switch in the aluminium foil and leave to develop at ambient temperature for 30 minutes. Note the time that the switch needs rinsing on the top of the aluminium foil using a permanent marker.
7. Repeat with the rest of the switches.
8. When the developing time is finished remove the switch from the foil and rinse for 2 minutes under the tap, running the fingers down the switch every 20 seconds.

The hair must be rinsed completely. If any bleach is left in, it will continue to develop.

9. Lay the switch down on the edge of the sink and using the WIDE teeth of a Matador Sawcut No4 comb; carefully comb the tangles out of the switch. Start at the tip end and work up slowly to the root. Once all the tangles have been combed out finish with the NARROW teeth of the comb.
10. Run the first and middle finger down the switch and dry at an ambient temperature overnight.

Second bleach application . . . Repeat steps 1-10 above and once completed wash and rinse the hair swatches completely to remove any residual bleach.

Results

| Surfactant | Total Conc (w/w %) | pH | Soak Time | Soak Temp | Hair Type |
|---|---|---|---|---|---|
| SLES - Texapon N71 | 1 | 7 | 1 Hr | 37 Deg C. | 2 x Bleached then Coloured Black |
| JBR425 - Jeneil | 1 | 7 | 1 Hr | 37 Deg C. | 2 x Bleached then Coloured Black |
| SLES/JBR425 (50:50 mix) | 1 | 7 | 1 Hr | 37 Deg C. | 2 x Bleached then Coloured Black |

| Surfactant mix | Absorbance at 522 nm |
|---|---|
| SLES- Texapon N71 | 3.9463 |
| JBR425 | 3.0079 |
| SLES/JBR425 50:50 mix | 3.651 |

The data shows that the amount of dye released into solution, from the dyed hair swatch, at the end of the process, is significantly greater for the SLES based surfactant system. Replacing the SLES with rhamnolipid significantly reduces the amount of dye loss from hair during the hair wash process with the rhamnolipid, and consequently increases the lifetime of a hair dye.

The invention claimed is:

1. A method of protecting a coloured or dyed substrate from dye transfer during exposure to an aqueous cleansing solution,
    the method comprising the step of treating said dyed or coloured substrate with a composition comprising a surfactant system,
    wherein said surfactant system comprises a glycolipid biosurfactant in the range 50-100 wt. %, and
    wherein said surfactant system is a total surfactant content of the composition.
2. A method according to claim 1 wherein the method further comprises the step of applying a dye to the substrate.
3. A method according to claim 1 wherein the method comprises the step of applying an aqueous solution comprising the composition to the substrate for a time period of 1 minute to 2 hours before rinsing.
4. A method of dyeing a substrate, the method comprising the steps of
    a. Applying a dye to the substrate and,
    b. Applying to the substrate a composition comprising a surfactant system comprising 50-100 wt. % glycolipid biosurfactant, wherein said surfactant system is a total surfactant content of the composition.
5. A method according to claim 4 wherein step b. follows step a.
6. A method according to claim 3 comprising the further step of rinsing the applied dye and/or glycolipid biosurfactant from the substrate using water.
7. A method according to claim 1 wherein the substrate is a fabric and/or human hair.
8. A method according to claim 1 wherein the glycolipid biosurfactant comprises a rhamnolipid or a sophorolipid.
9. A method according to claim 8 wherein the rhamnolipid comprises a ratio of mono-rhamnolipid:di-rhamnolipid (R1:R2) such that R2 is always greater in proportion by weight to R1.
10. A method according to claim 9 wherein the rhamnolipid is 100 wt. % di-rhamnolipid (R2).
11. A kit for dyeing hair comprising a dye composition and a composition comprising a glycolipid biosurfactant according to claim 1.

* * * * *